(12) United States Patent
Burgos-Rivera et al.

(10) Patent No.: US 10,881,326 B1
(45) Date of Patent: Jan. 5, 2021

(54) WEARABLE SAFETY DEVICE

(71) Applicants: Miramique Modesty Burgos-Rivera, Land O'Lakes, FL (US); Miriam Soto-Burgos, Land O'Lakes, FL (US); Juan Alfonso Rivera, Land O' Lakes, FL (US)

(72) Inventors: Miramique Modesty Burgos-Rivera, Land O'Lakes, FL (US); Miriam Soto-Burgos, Land O'Lakes, FL (US); Juan Alfonso Rivera, Land O' Lakes, FL (US)

( * ) Notice: Subject to any disclaimer, the term of this patent is extended or adjusted under 35 U.S.C. 154(b) by 0 days.

(21) Appl. No.: 16/365,083

(22) Filed: Mar. 26, 2019

Related U.S. Application Data

(60) Provisional application No. 62/649,250, filed on Mar. 28, 2018.

(51) Int. Cl.
| | | |
|---|---|---|
| *G08B 1/08* | (2006.01) |
| *A61B 5/11* | (2006.01) |
| *A61B 5/0205* | (2006.01) |
| *A61B 5/00* | (2006.01) |
| *G06F 1/16* | (2006.01) |
| *A61B 5/021* | (2006.01) |
| *A61B 5/024* | (2006.01) |

(52) U.S. Cl.
CPC .......... *A61B 5/1112* (2013.01); *A61B 5/0205* (2013.01); *A61B 5/6826* (2013.01); *A61B 5/6843* (2013.01); *A61B 5/021* (2013.01); *A61B 5/02405* (2013.01); *G06F 1/163* (2013.01)

(58) Field of Classification Search
CPC ... A61B 5/1112; A61B 5/0205; A61B 5/6826; A61B 5/6843; A61B 5/021; A61B 5/02405; G06F 1/163
USPC ...................................................... 340/539.11
See application file for complete search history.

(56) References Cited

U.S. PATENT DOCUMENTS

| | | | |
|---|---|---|---|
| 2013/0014706 A1* | 1/2013 | Menkes ............... | A01K 27/009 119/859 |
| 2014/0120872 A1* | 5/2014 | Amis ................. | H04M 1/72541 455/411 |
| 2014/0282059 A1* | 9/2014 | Oh ........................ | G06F 3/0481 715/744 |
| 2015/0065082 A1* | 3/2015 | Sehgal ................. | G08B 25/016 455/404.2 |
| 2016/0116941 A1* | 4/2016 | Kuwabara ............... | G06F 1/163 361/679.03 |

(Continued)

*Primary Examiner* — Naomi J Small
(74) *Attorney, Agent, or Firm* — John Rizvi; John Rizvi, P.A.—The Patent Professor®

(57) ABSTRACT

There is disclosed a wearable, personal safety device that can be activated to silently send an alarm along with a video and an audio feed, in real time, to a monitoring authority. The personal safety device includes a support member for positioning the personal safety device on a user and housing affixed to the support member and containing a main circuit board and a camera system connected to the main circuit board. The camera system includes both video and audio components. An alarm or activation button is movably mounted on the housing and in selective contact with the main circuit board such that when the activation button is depressed relative to the housing, a silent alarm along with a video and audio feed is sent to the remote monitoring system. The personal safety device can further include a global positioning unit and/or a heart rate monitor module.

18 Claims, 7 Drawing Sheets

(56) References Cited

U.S. PATENT DOCUMENTS

2017/0309149 A1* 10/2017 Kaura ................ G06K 9/00778

* cited by examiner

US 10,881,326 B1

WEARABLE SAFETY DEVICE

CROSS-REFERENCE TO RELATED APPLICATION

This application claims the benefit of U.S. Provisional Patent Application Ser. No. 62/649,250, filed Mar. 28, 2018, which is incorporated herein in its entirety.

FIELD OF THE INVENTION

The present invention relates generally to personal safety devices, and more particularly, to a wearable safety device that allows a user to discretely notify safety services in the case of an emergency.

BACKGROUND OF THE INVENTION

People are sometimes subjected to many different types of dangers or attacks as they go about their daily lives. Thus, it is important in many emergency situations to be able to quickly and easily call for help. This is particularly true in extreme or dire situations such as impending assault, kidnapping, etc. Many people carry cell phones to call for help in case of emergencies and to give authorities the nature and location of the attack, but they are usually carried in pockets or purses rendering them incapable of quick deployment.

Other types of emergency devices are available that are quicker and easier to deploy. Many of these devices emit loud sounds in the form of piercing noises or screeching to dissuade an attacker and attract the attention of passersby. However, while these noisemakers are useful in public or reasonably crowded situations, they are of little or no use in remote or isolated area situations where most assaults typically occur and help is a distance away.

Both the use of cell phones and noisemaking type devices are not very discrete and unfortunately quite obvious to an assailant. In some isolated situations, the use of these devices may actually enrage or make the assailant even more aggressive and harmful. Further, in the absence of any witnesses, later proving the nature of the attack and the identity of the assailant is often difficult.

Danger need not only be limited to external attacks or kidnapping type incidents. Situations such as heart attacks, accidents in remote areas, of just getting lost generally require the ability to summon help. Personal medical emergencies particularly require the need to quickly and easily summon help and provide responding authorities with an accurate location of the injured or incapacitated party.

Accordingly, there is an established need for a simple personal safety device which solves at least one of the aforementioned problems.

SUMMARY OF THE INVENTION

The present invention is directed to a discrete personal safety device that can be activated to silently send an alarm signal along with a video and audio feed, in real time, to a monitoring authority. The personal safety device includes a support member for positioning the personal safety device on a user and housing containing a main circuit board and a camera system connected to the main circuit board. The main circuit board includes a wireless communications system for contacting a remote monitoring authority or service. The camera system includes both video and audio components. An alarm or activation button is movably mounted on the housing and is in selective contact with the main circuit board such that when the activation button is depressed relative to the housing, a silent alarm along with a video and audio feed is sent to the remote monitoring system. The personal safety device also includes a global positioning unit and a heart rate monitor module connected to the main circuit board. A battery system is provided in the housing to power the various components and a vibrator motor is mounted in the housing to signal to the user when the system has been activated.

Introducing a first embodiment of the invention, the present invention consists of a personal safety device for discretely sending a signal to a monitoring system, comprising:

a support member mountable on a user's body;
a housing attached to the support member;
an activation button movably mounted in the housing;
a camera system mounted on the housing and including a video camera and an audio system configured to capture video and audio, respectively, from the surroundings of the personal safety device;
a main circuit board contained within the housing and including a wireless communication system;
a battery system connected to the camera system, the main circuit board and the activation button, the main circuit board being in electrical communication with the activation button and the camera system, such that activation of the activation button causes the wireless communication system to send an alarm signal to a remote monitoring system, the alarm signal including real time video and audio feeds from the camera system.

In a second aspect, the personal safety device can further include a global positioning system connected to the main circuit board, wherein activation of the activation button causes the wireless communication system to transmit the personal safety devices position to the remote monitoring system.

In another aspect, the personal safety device can further include a vibrator motor associated with the activation button and the main circuit board such that activation of the activation button causes the vibrator motor to vibrate the housing.

In another aspect, the personal safety device can further include a heart rate monitor module connected to the main circuit board for monitoring a user's vital functions.

In another aspect, the support member can be a flexible ring.

In another aspect, the support member can be a bracelet or a necklace.

In another aspect, the support member can be a collar.

In another aspect, the activation button and camera system can be covered with a transparent cover.

In another aspect, the transparent cover can include a concealing design.

In another aspect, the activation button is covered by a material that conceals the activation button, and a camera lens is covered by a material that conceals the camera lens.

In another aspect, the support member includes a ring-shaped core that extends through the support member between the main circuit board and the battery system, providing support for the housing and acting as a conduit for transmitting power from the battery system to the main circuit board, and wherein the main circuit board and the battery system are supported on a lower partition of the housing and the activation button and the camera system are supported on an upper partition of the housing.

In another aspect, the personal safety device further includes a vital function monitor module connected to the main circuit board for monitoring a user's vital functions, such that authorities are automatically contacted when the vital functions stray out of pre-programmed parameters.

In another aspect, the main circuit board communicates wirelessly with a nearby personal electronic device to send both audio and video feeds along with location and vital sign data to monitoring authorities.

These and other objects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, where like designations denote like elements, and in which.

Like reference numerals refer to like parts throughout the several views of the drawings.

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Shown throughout the figures, the present invention is directed toward a convenient personal safety device that is capable of discretely and quickly summoning authorities for help in threatening and/or dangerous situations.

Figure 1:
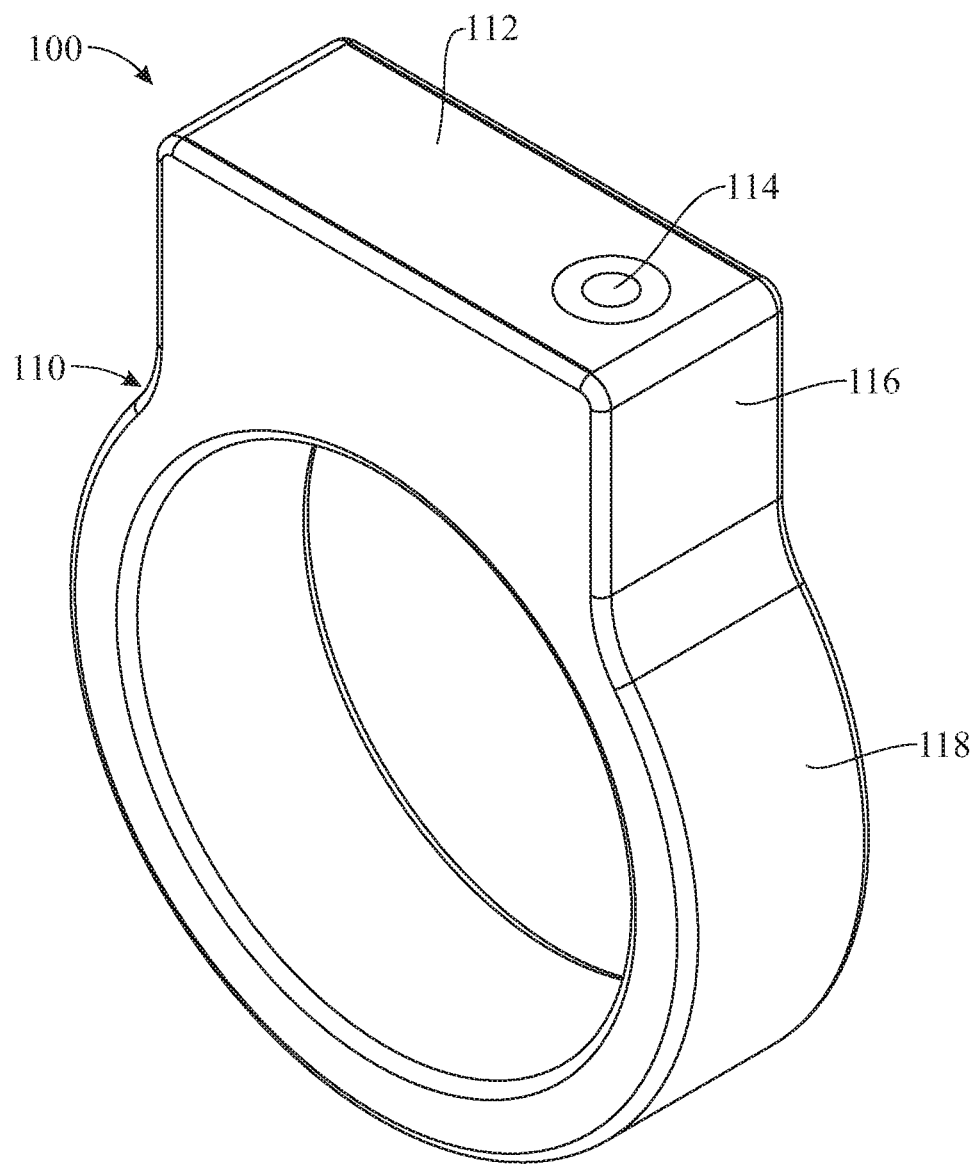
FIG. 1 presents a perspective view of a ring-type, wearable safety device in accordance with a first embodiment of the present invention.
Figure 2:
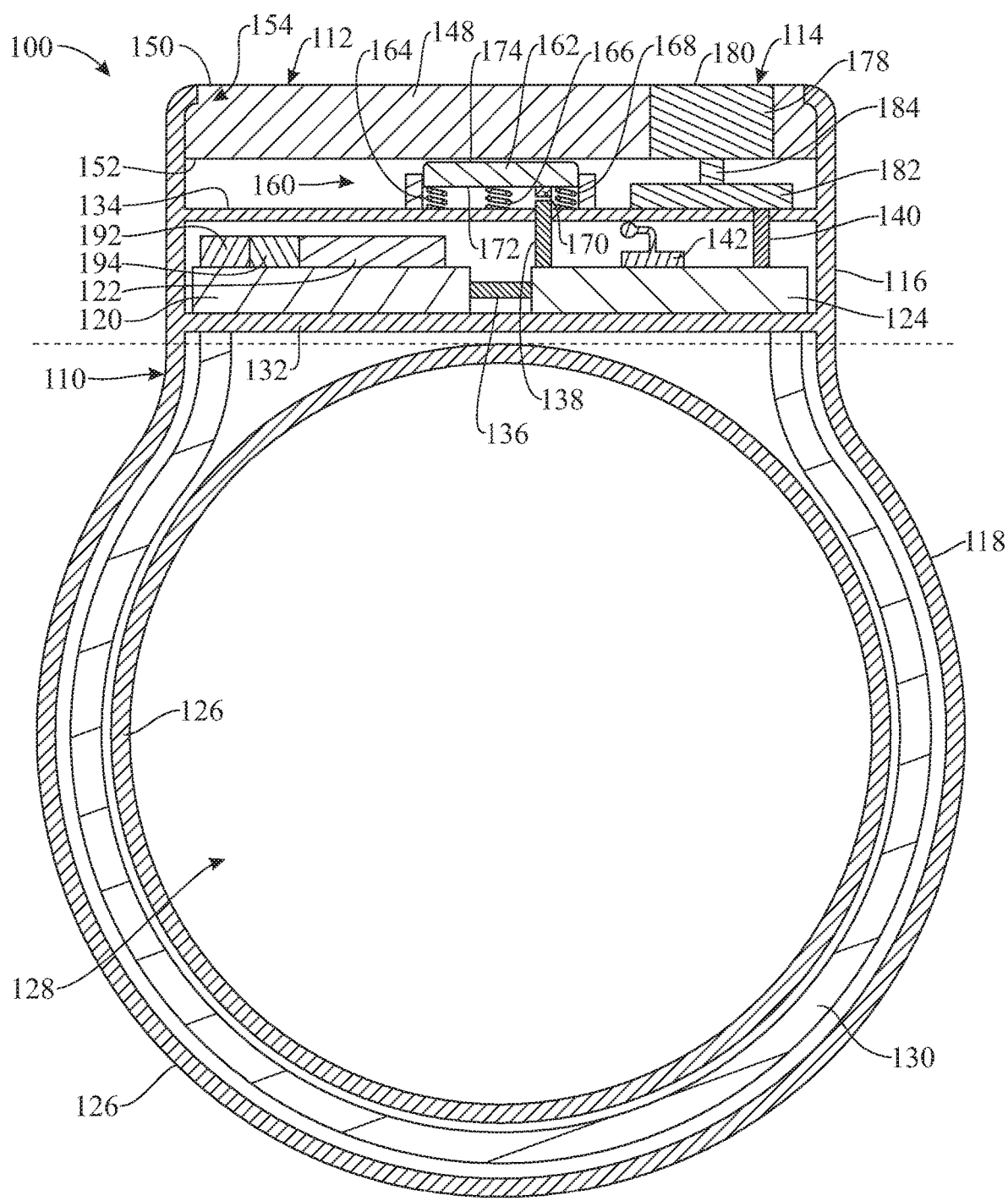
FIG. 2 presents a cross-sectional front elevation view of the ring-type wearable safety device of FIG. 1.

Referring initially to FIGS. 1 and 2, a personal safety device 100 is illustrated in accordance with an exemplary embodiment of the present invention, configured as a ring-shaped safety device. As shown, the personal safety device 100 generally includes ring-shaped body portion 110, an alarm button 112 and a camera system 114. The ring-shaped body portion 110 includes a housing 116 and a support ring 118 for comfortably maintaining the housing 116 on a finger of a user. In some embodiments, the ring-shaped body portion 100 can be formed from a comfortable and flexible material to encourage long term wear and allow for size growth. One such material is a pliable, silicone material which is both flexible and stretchable and renders the housing 116, and thus the entire system, waterproof. While not specifically shown, the alarm button 112 and the camera system 114 are hidden from view and may be covered with a glass or an acrylic material, embellished with a variety of decorative elements or scenes, to conceal the alarm button 112 and the camera lens 114, and thus the nature of the personal safety device 100, from an assailant.

Referring now specifically to FIG. 2, as shown, a main circuit board 120 is retained within the housing 116. The main circuit board 120 performs a variety of functions and includes a processor for coordinating and enabling the functions of the personal safety device 100. The main circuit board 120 further includes a radio frequency (RF) communications module for communicating with a cell phone via Bluetooth® or the internet via a Wi-Fi™ technology in order to contact authorities and may additionally include a vital signs or heart rate monitor, discussed below, to provide authorities with personal health data and status. A global positioning system or (GPS) unit 122 is also contained within the housing 116 and connected to the main circuit board 120 to give authorities the exact location of the person in distress. A battery system 124 is contained within the housing 116 and connected to the main circuit board 120, the camera system 114 and the GPS unit 122 to power them. Preferably, the battery system 124 is rechargeable and is easily connected to a wired recharging system through a port (not shown) or can be recharged via a wireless charging type device. Alternatively, the battery system 124 may include a long-lasting tritium type battery.

As shown, the body portion 110 includes a soft, generally flexible outer skin 126 defining a finger ring opening 128 through the support ring 118 for receipt of a user's finger. A ring-shaped core 130 extends through the outer skin 126 and extends between the main circuit board 120 and the battery system 124. The core 130 provides support for the housing 116. In some embodiments, the core 130 may provide a conduit for transmitting power from the battery system 124 to the main circuit board 120. The housing 116 is provided with a pair of internal first and second partitions 132 and 134 for support of the various components. In the present embodiment, the main circuit board 120 and the battery system 124 are supported on the lower or first partition 132 while the alarm button 112 and the camera system 114 are supported on the upper or second partition 134.

A first conduit or cable 136 connects the main circuit board 120 to the battery system 124 and a second conduit or cable 138 connects the alarm button 112 to the battery system 124 and thus to the main circuit board 120. A third conduit or cable 140 is also provided and connects the camera system 114 to the battery system 124 and main circuit board 120. A ground system 142 is connected to battery system 124 and the housing 116.

The alarm button 112 includes a body portion 148 having an upper engagement surface 150 and a lower contact surface 152. The body portion 148 of the alarm button 112 is supported within an upper opening 154 in the housing 116. A spring-biased switching mechanism 160 is secured on the upper or second partition 134 and connects the alarm button 112 to the second conduit or cable 138 and thus to the main circuit board 120 and battery system 124. Specifically, the switching mechanism 160 includes an upper block 162 movably supported on the second partition 134 by a series of springs 164, 166 and 168. A contact member 170 is provided on a lower side 172 of the upper block 162 and contacts the second conduit 138 when the alarm button 112 is depressed to activate the system as described in more detail hereinbelow. An upper side 174 of the upper block 162 is in engagement with the lower contact surface 152 of the alarm button 112 such that depression of the alarm button 112 drives the contact 170 into engagement with the second conduit or cable 138 to activate the system.

The camera system 114 is provided to supply both video and audio information to contacted authorities. The camera system 114 includes a main camera body 178 having a hidden camera lens 180. As noted hereinabove, the camera system 114 may be covered with decorative or informative coverings so as to conceal the camera lens 180 from assailants. While not specifically shown, the main camera body 178 additionally includes a hidden microphone for collecting audio data. The camera system 114 further includes an audio-visual module or system 182 which is connected to the main camera body 178 by a fourth conduit or cable 184 and to the battery system 124, and thus the main circuit board 120, by the third conduit 140. The camera system 114 is of a solid-state variety and is entirely silent with the audio system preferably only transmitting audio and not receiving audio to avoid attracting the attention of the assailant. Additionally, the video system of the camera system 114 is non-illuminated so as to also not draw the attention of the assailant.

Figure 3:
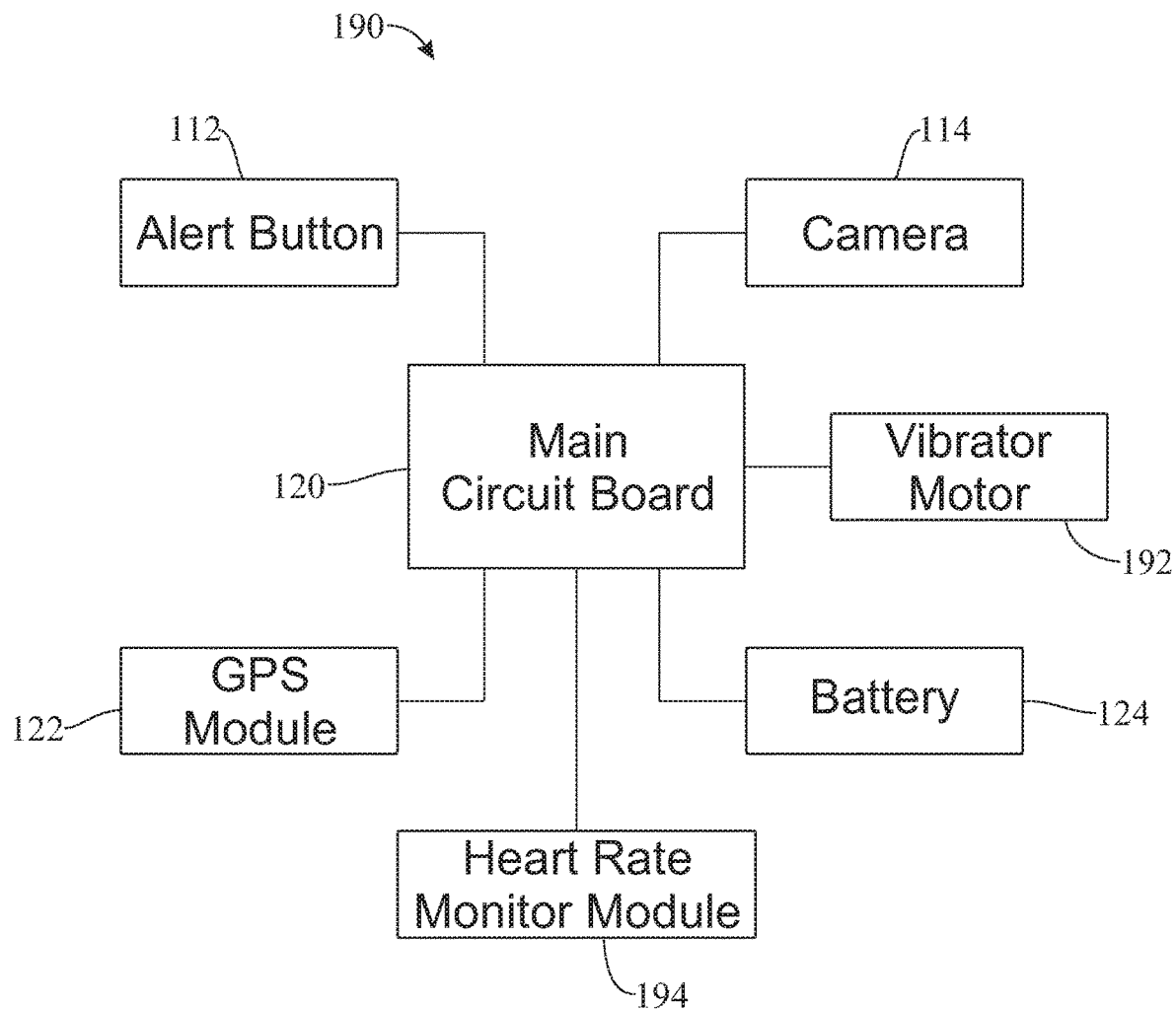
FIG. 3 presents a block diagram of electrical components of the ring-type, wearable safety device of FIG. 1.

Referring for the moment to FIG. 3, there is illustrated a block diagram 190 of the various connections of the components of the personal safety device 100. As can be seen, the main circuit board 120 is connected to both the alert or alarm button 112 and the camera system 114. The main circuit board 120 is also connected to the battery system 124 and the GPS unit 122 as described hereinabove. As further described hereinabove, the personal safety device 100 additionally includes a vibrator motor 192 which vibrates upon activation of the alarm button 112 to silently and discretely confirm to the user that the system has been activated and that the call for help from authorities has been communicated and received. Additionally, a heart rate monitor module 194 is connected to the main circuit board 120 and continually monitors the user's heart rate and other vital functions. These vital functions provide the authorities of the level of distress and harm during attack. These continually monitored vital functions may also trigger the main circuit board 120 to contact the authorities should the vital functions stray out of pre-programmed parameters during health emergencies such as, for example, heart attack, stroke, other injury indicated by increased heart rate, etc.

Turning to FIGS. 1-5, the use and operation of the personal safety device 100 will now be described. Initially, with regard to FIGS. 1 and 2, the personal safety device 100, including the battery system 124, is fully charged through a port (not shown) in the housing 116 or via wireless charging system and any personal data loaded into the main circuit board 120. Data such as personal identification, safety device 100 identifying data, health data and emergency contact data can be preloaded into the personal safety device 100 either by the user personally through a home computer or by the seller at the time of purchase and registration of the personal safety device 100. The data can be changed by the user at any time through a dedicated website.

In use, the user inserts their finger through the finger ring opening 128. As noted, the support ring 118 is formed of a material that is both comfortable and flexible to conform to the user's finger. This ensures the user will more likely wear the personal safety device 100 constantly and allows the support ring 118 to expand as the user's finger swells during the day or grows or shrinks as the user ages. The personal safety device 100 can be turned on and off by depressing the alarm button 112 for a specified duration. Alternatively, the personal safety device 100 can be on all the time as long as there is battery power or while charging. This allows the user to grab and activate the device at home while not wearing the personal safety device 100 during an emergency such as a break in.

In another example, the alarm may be activated by depression without being deactivatable after being activated, eliminating the possibility of an assailant turning off the device once the alarm is activated. This prevents an assailant from canceling the deployment of emergency response services, as well as canceling further transmission of data.

Once activated, the personal safety device 100 monitors the user's vital signs. Should, at any time, the heart rate monitor module (FIG. 3) detect that the user's vital signs move out of a predetermined range, as in the case of a heart attack or stroke, the main circuit board 120 will send a wireless signal to monitoring authorities containing the vital signs data as well as a location determined by the on-board GPS unit 122. The monitoring authorities can then determine if help is needed and immediately dispatch medical assistance to the user's location. Additionally, the vibrator motor 192 will vibrate indicating to the user that they are undergoing distress and to seek out immediate assistance if available. The vibration from the vibrator motor 192 tells the user that a signal and data have been sent to the monitoring authorities and that help is on the way.

The personal safety device 100 can also be programmed to constantly transmit a person's location to a dedicated site. Alternatively, the dedicated site can be used to wirelessly and silently activate the personal safety device 100 to give a caregiver or parent a wearer's location and vital signs. In this manner, should an elderly person suffering from dementia, Alzheimer's, etc. wander off or be lost, the caretaker can locate them and the monitoring authorities send police to retrieve and aid the person. This also can be used to monitor children and ensure that they are safe and arrive home safely.

Figure 4:
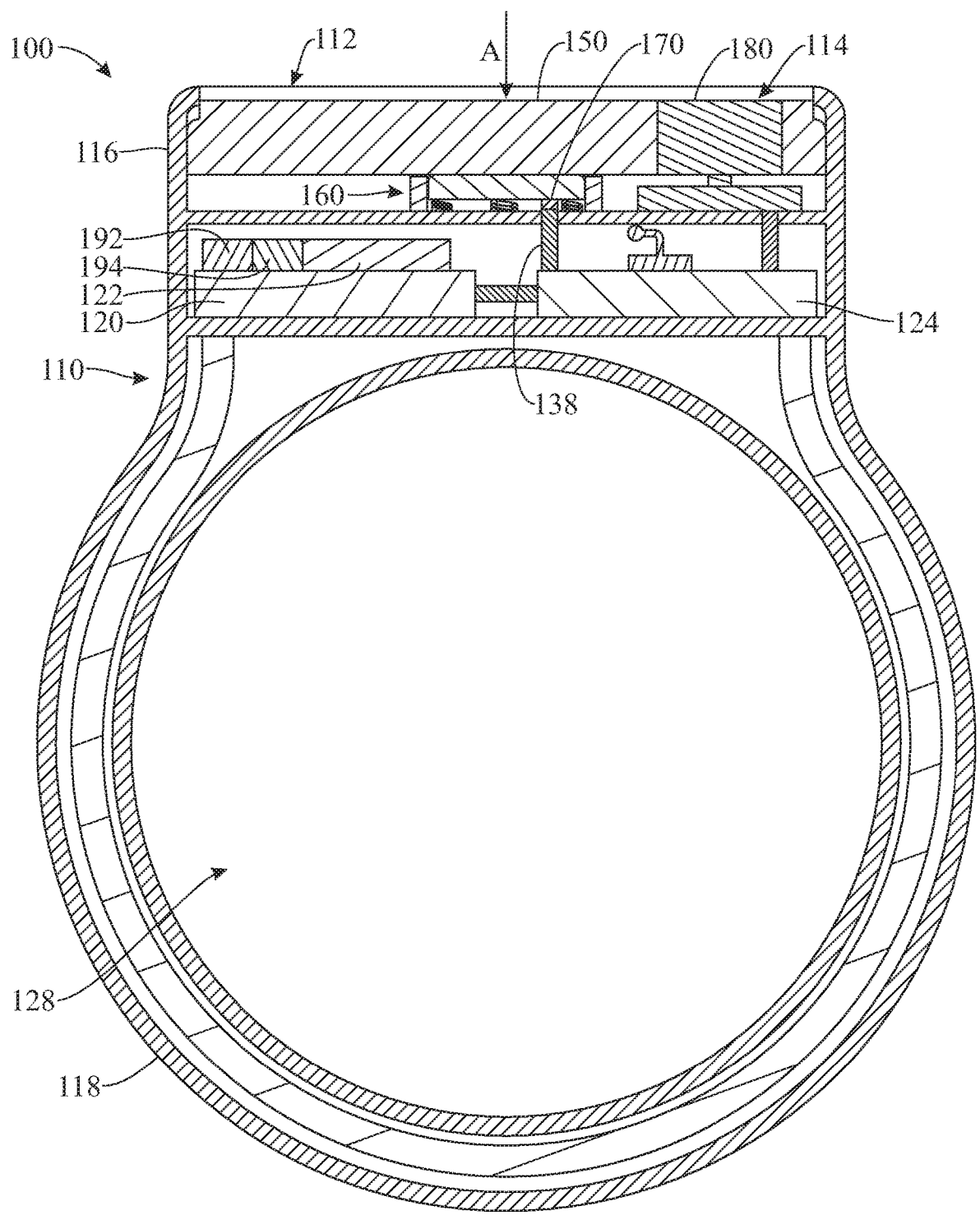
FIG. 4 presents a cross-sectional front elevation view similar to FIG. 2, with an actuation button of the ring-type, wearable safety device in a depressed or activated condition.
Figure 5:
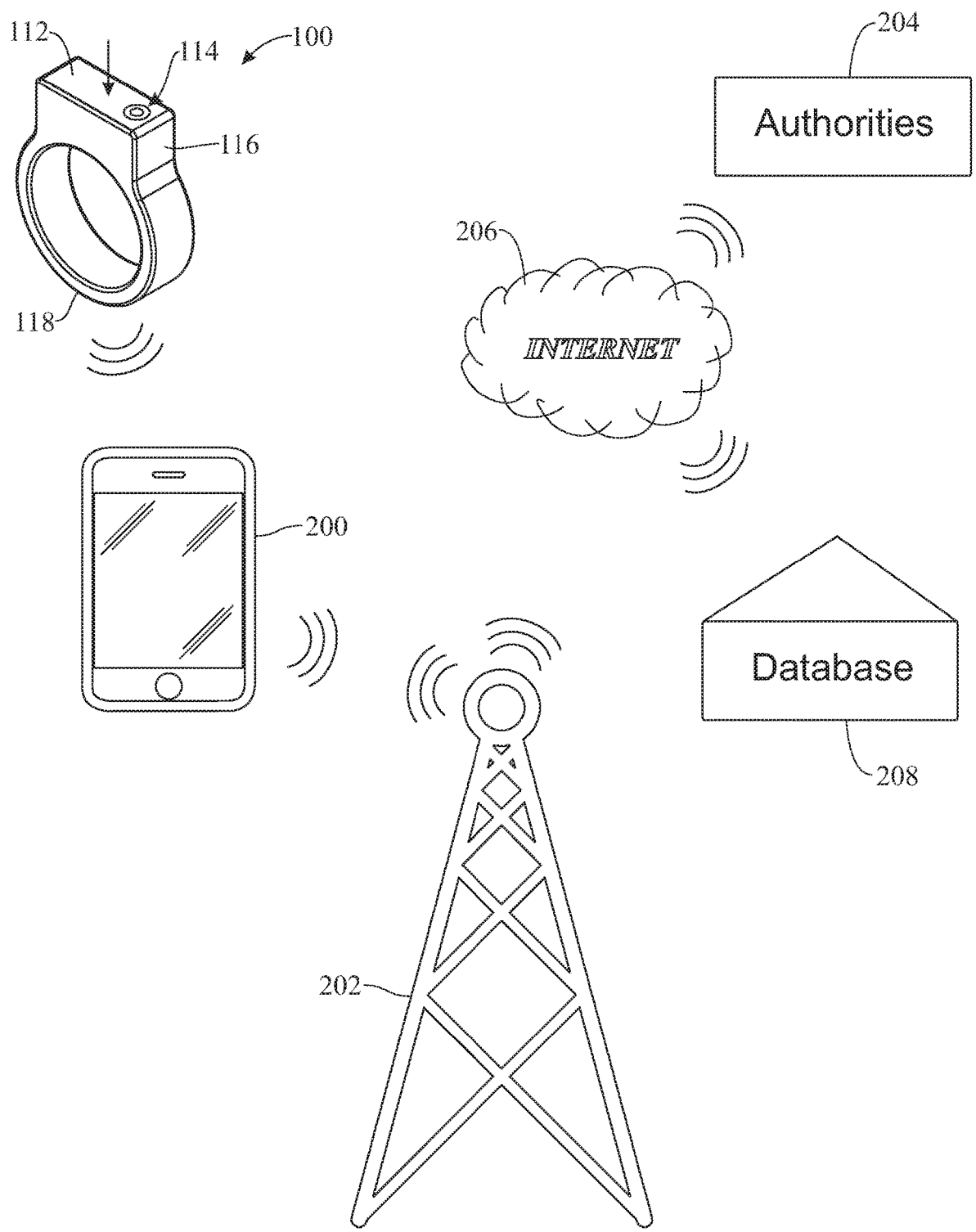
FIG. 5 presents a diagrammatical view of a method of operation of the ring-type wearable safety device of FIG. 1.

Referring to FIGS. 4 and 5, in the event that a person wearing the personal safety device 100 comes under attack, either through assault or a kidnapping type event, the person can signal for help. In this instance, the person depresses the alarm button 112 in the direction of arrow "A" for a predetermined period of time, such as, but not limited to, 3 consecutive seconds, as shown in FIG. 4. The vibrator motor 192 (FIG. 3) will immediately begin to vibrate for a specific amount of time (e.g., 5 seconds) informing the user that a signal for help has been sent to the monitoring authorities. Vibration of the vibrator motor 192 also informs the user that the video/audio system associated with the camera system 114 has been activated and that the authorities can see and hear what is occurring. Due to the one-way nature of the audio system, the system is virtually silent and the assailant (s) are not made aware that a call for help has been sent. Additionally, because the alarm button 112 and the camera system 114 are shielded from view, no visual clue is given off to the assailants that any security system has been activated further aiding to the assailed user's safety.

In another example, once the button 112 is pressed, the button 112 does not have to be swiped to the right for activation, and it only needs to be depressed for 2-3 consecutive seconds. The platform of the alarm button 112 may be made wide enough to accommodate a finger and transmit a signal, regardless of what portion of the emergency button is pressed.

Should the alarm button 112 be accidentally depressed for the aforementioned predetermined period of time (e.g. 3 seconds), the vibration additionally informs the user of the inadvertent activation and the user can contact the monitoring authorities to notify them of the false alarm.

As best shown in FIG. 5, once activated, the main circuit board 120 communicates wirelessly, such as through nearby Wi-Fi access or via a Bluetooth signal sent to a nearby cell phone 200 or other communications device, to send both the audio and video feeds along with the location and vital signs data to the monitoring authorities. The cell phone 200 connects wirelessly with a cell tower 202 which then sends a signal to a remote computer or control unit, hereinafter referred to generally as the authorities 204, such as over the Internet 206 or another computer network. Alternatively, as noted above, the personal safety device 100 communicates directly through a Wi-Fi signal to the Internet 206 which then communicates with the authorities 204. The authorities 204 can also compare the vital signs and other pre-loaded data provided by the user and contained in the user's database 208 to determine the severity of the situation. Help in the form of police, ambulance, or other first responders are then immediately dispatched to the user's location. The assailants are never made aware of any call for help rendering the personal safety device a silent alarm type system. Should the personal safety device 100 become a popular and widely used personal silent alarm type safety system, this alone could cut down on assaults as the assailants may never know if a call for help has been sent and proof of their identity transmitted to authorities.

Figure 6:
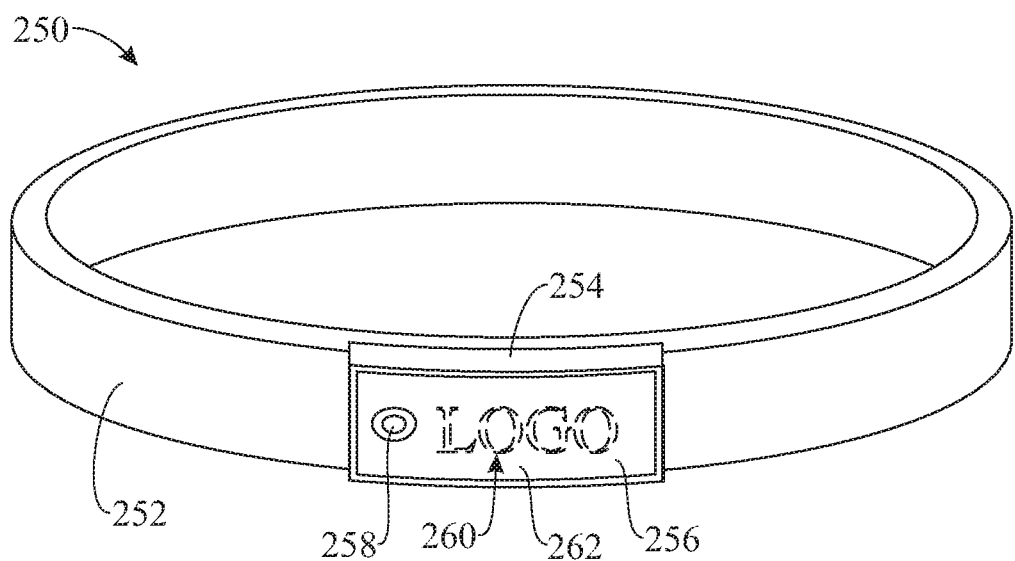
FIG. 6 presents a perspective view of a bracelet-type, wearable safety device in accordance with a second embodiment of the present invention.

Referring to FIG. 6, there is illustrated a second embodiment of a personal safety device 250 in accordance with the invention. The personal safety device 250 is a bracelet type safety device and is identical to the personal safety device 100 described hereinabove with the exception of a wrist strap or bracelet 252 in lieu of the support ring 118 of the personal safety device 100. It must be noted that alternative embodiments are contemplated in which the personal safety device (e.g., the personal device 250) may be large enough to be used as a necklace instead of a bracelet. The personal safety device 250 includes a housing 254 connected to or mounted on the bracelet 252 and an alarm button 256 and camera system 258 retained within the housing 254. The housing 254 additionally contains a main circuit board, a battery system, a GPS unit, a switching mechanism and vibrator motor identical to those described hereinabove with regard to the personal safety device 100. The personal safety device 250 operates identical to the personal safety device 100 described hereinabove but may be more comfortable for those users who prefer to wear a bracelet rather than a ring.

As noted above, the personal safety device 100 can include a glass or acrylic cover over the alarm button 112 and camera system 114 to conceal them from any assailants. Likewise, the personal safety device 250 may have decorations in the form of various indicia, logos or custom artwork 260 imprinted or otherwise adhered or etched into a glass or acrylic cover 262 positioned over the alarm button 256 and the camera system 258. It should be noted that any cover 262 will be fully transparent, at least in the area covering the camera system 258, so as to not impede or degrade any images transmitted to authorities.

Figure 7:
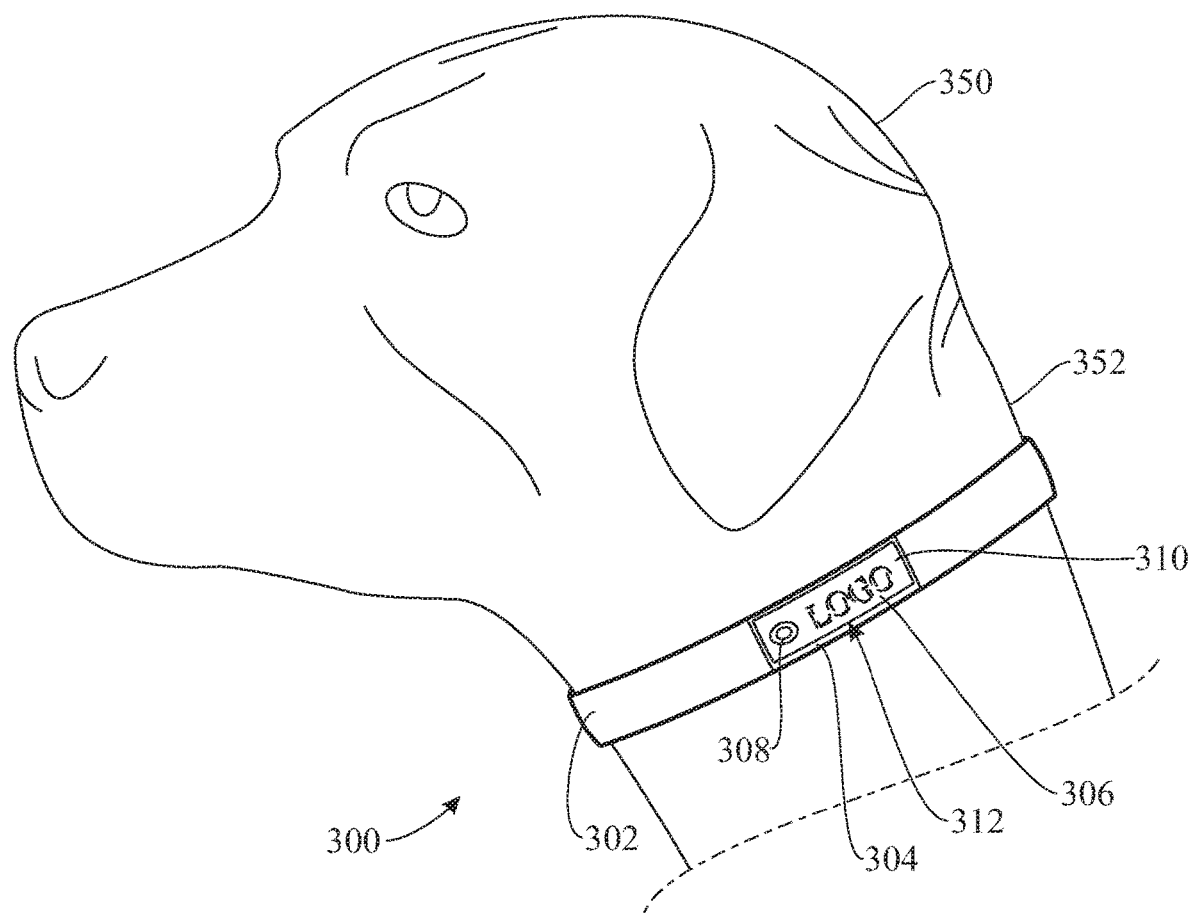
FIG. 7 presents a pet collar type, wearable safety device in accordance with a third embodiment of the present invention.

Turning now to FIG. 7, the disclosed personal safety systems can be configured for use with pets such as dogs, cats, etc. where it is desirable to stay aware of a pet's location and, more importantly, the pet's health status. A personal or pet safety device 300 is provided for use with pets such as a dog 350 and generally includes a ring type dog collar 302 having a housing 304 secured to the dog collar 302. The pet safety device 300 functions similar to those described hereinabove to transmit dog's 350 location and vital signs to a user or owners database on a website. The system can be always on or remotely activated by the owner, through the internet or cell service, to monitor the pet. The pet safety device 300 is adjustable and is designed to be worn about a neck 352 of a pet such as the dog 350.

The housing 304 of the pet safety device 300 includes a main circuit board, a battery system, a GPS unit and a heart rate monitor module (not shown) identical to those described hereinabove with regard to the personal safety device 100. The pet safety device 300 may additionally include a switching mechanism and vibrator motor also not shown. Further, the pet safety device may include an alarm button 306 and a camera system 308. The alarm button 306 allows a good samaritan who finds the dog to activate the pet safety device 300 and the camera system 308 allows the owner or authorities to better determine where the dog is, what its emergency is like and the identity of persons who may have taken the dog 350. In some embodiments, the pet safety device 300 can transmit a notification of the lost pet, such as over the Internet 206 or another computer network, with the notification including a description of the pet being sent out to all veterinary offices and pet shelters in the area closest to the where the pet is traced to. Like the embodiments described hereinabove, the housing 304 may include a covering 310 containing indicia 312 in the form of hiding material over the camera system 308 or instructions for activating the system to assist a good samaritan in returning the dog 350 to its rightful owner.

In this manner, the disclosed safety devices, including the personal safety devices 100 and 200 and the pet safety device 300, enable a user to silently and discretely notify authorities of an emergency situation and provide the authorities not only with exact, real time GPS location and vital systems data but also a real time audio and video feed of an assault or emergency situation to better enable the authorities to determine what type of response is needed, be it police, medical, etc.

In another example configuration, the disclosed device 300 may have interchangeable hardware components. For example, hardware components of one accessory may be replaced with hardware components of another accessory, allowing a user to select different designs or form factors for the accessory. For example, the components above the dashed line in FIG. 2 may be removed.

Removing the components may be done in various ways. In one method, a cap or lid of the accessory may be opened such that the components may be removed and replaced. In another example, an entire upper portion of the accessory (e.g. rectangular portion in FIG. 2) may be removably attached.

Since many modifications, variations, and changes in detail can be made to the described preferred embodiments of the invention, it is intended that all matters in the foregoing description and shown in the accompanying drawings be interpreted as illustrative and not in a limiting sense. Furthermore, it is understood that any of the features presented in the embodiments may be integrated into any of the other embodiments unless explicitly stated otherwise. The scope of the invention should be determined by the appended claims and their legal equivalents.

What is claimed is:

1. A personal safety device for discretely sending a signal to a monitoring system, comprising:
   a support member mountable on a user's body;
   a housing attached to said support member;
   an activation button movably mounted in said housing;
   a camera system mounted on said housing and including
      a video camera and an audio system configured to capture video and audio, respectively, from the surroundings of the personal safety device;
   a main circuit board contained within said housing and including a wireless communication system; and
   a battery system connected to said camera system, said main circuit board and said activation button, said main circuit board being in electrical communication with said activation button and said camera system, such that activation of said activation button causes said wireless communication system to send an alarm signal to a remote monitoring system, said alarm signal including real time video and audio feeds from said camera system; and
   wherein the personal safety device further includes a vibrator motor associated with the activation button and the main circuit board such that activation of the activation button causes the vibrator motor to vibrate the housing; and
   wherein the activation button and camera system are covered with a concealing cover, wherein opposing edges of the cover are fixed to the housing.

2. The personal safety device of claim 1, wherein the personal safety device further includes a global positioning system connected to the main circuit board, wherein activation of the activation button causes the wireless communication system to transmit the personal safety device's position to the remote monitoring system.

3. The personal safety device of claim 1, wherein the personal safety device further includes a vital function monitor module connected to the main circuit board for monitoring a user's vital functions.

4. The personal safety device of claim 1, wherein the support member is a finger ring.

5. The personal safety device of claim 1, wherein the support member is a bracelet.

6. The personal safety device of claim 1, wherein the support member is a necklace.

7. The personal safety device of claim 1, wherein the support member is a collar.

8. A personal safety device for discretely sending a signal to a monitoring system, comprising:
   a support member mountable on a user's body;
   a housing attached to said support member;
   an activation button movably mounted in said housing;
   a camera system mounted on said housing and including
      a video camera and an audio system configured to capture video and audio, respectively, from the surroundings of the personal safety device;
   a main circuit board contained within said housing and including a wireless communication system, wherein the wireless communication system sends the signal without requiring an intermediate personal electronic device;
   a battery system connected to said camera system, said main circuit board and said activation button, said main circuit board being in electrical communication with said activation button and said camera system, such that activation of said activation button causes said wireless communication system to send an alarm signal to a remote monitoring system, said alarm signal including real time video and audio feeds from said camera system; and
   wherein the personal safety device further includes a global positioning system connected to the main circuit board, wherein activation of the activation button causes the wireless communication system to transmit the personal safety device's position to the remote monitoring system; and
   wherein the personal safety device further includes a vibrator motor associated with the activation button and the main circuit board such that activation of the activation button causes the vibrator motor to vibrate the housing; and
   wherein the activation button and camera system are covered with a concealing cover, wherein opposing edges of the cover are fixed to the housing.

9. The personal safety device of claim 8, wherein the personal safety device further includes a vibrator motor associated with the activation button and the main circuit board such that activation of the activation button causes the vibrator motor to vibrate the housing.

10. The personal safety device of claim 8, wherein the personal safety device further includes a vital function monitor module connected to the main circuit board for monitoring a user's vital functions.

11. The personal safety device of claim 8, wherein the activation button and camera system are covered with a concealing cover.

12. A personal safety device for discretely sending a signal to a monitoring system, comprising:
   a support member mountable on a user's body;
   a housing attached to said support member;
   an activation button movably mounted in said housing;
   a camera system mounted on said housing and including
      a video camera and an audio system configured to capture video and audio, respectively, from the surroundings of the personal safety device;
   a main circuit board contained within said housing and including a wireless communication system;
   a battery system connected to said camera system, said main circuit board and said activation button, said main circuit board being in electrical communication with said activation button and said camera system, such that activation of said activation button causes said wireless communication system to send an alarm signal to a remote monitoring system, said alarm signal including real time video and audio feeds from said camera system;
   wherein the personal safety device further includes a global positioning system connected to the main circuit board, wherein activation of the activation button causes the wireless communication system to transmit the personal safety device's position to the remote monitoring system; and wherein the activation button is covered by a material that conceals the activation button, and a camera lens is covered by a material that conceals the camera lens; and wherein the personal safety device further includes a vibrator motor associated with the activation button and the main circuit board such that activation of the activation button causes the vibrator motor to vibrate the housing; and wherein the opposing edges of the material covering the activation button and the camera lens are fixed to the housing.

13. The personal safety device of claim 12, wherein the support member includes a ring-shaped core that extends through the support member between the main circuit board and the battery system, providing support for the housing and acting as a conduit for transmitting power from the battery system to the main circuit board, and wherein the main circuit board and the battery system are supported on a lower partition of the housing and the activation button and the camera system are supported on an upper partition of the housing.

14. The personal safety device of claim 12, wherein the personal safety device further includes a vital function monitor module connected to the main circuit board for monitoring a user's vital functions, such that authorities are automatically contacted when the vital functions stray out of pre-programmed parameters.

15. The personal safety device of claim 12, wherein the main circuit board communicates wirelessly with a nearby personal electronic device to send both audio and video feeds along with location and vital sign data to monitoring authorities.

16. The personal safety device of claim 12, wherein the support member is a finger ring.

17. The personal safety device of claim 12, wherein the support member is a bracelet or necklace.

18. The personal safety device of claim 12, wherein hardware components of the personal safety device are interchangeably attached within the device.

* * * * *